(12) United States Patent
Birkbeck et al.

(10) Patent No.: US 10,787,627 B2
(45) Date of Patent: Sep. 29, 2020

(54) VETIVER ODORANT

(71) Applicant: Firmenich SA, Satigny (CH)

(72) Inventors: Anthony Alexander Birkbeck, Geneva (CH); Hervé Mosimann, Geneva (CH); Hervé Pamingle, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 15/764,350

(22) PCT Filed: Sep. 29, 2016

(86) PCT No.: PCT/EP2016/073267
§ 371 (c)(1),
(2) Date: Mar. 29, 2018

(87) PCT Pub. No.: WO2017/055458
PCT Pub. Date: Apr. 6, 2017

(65) Prior Publication Data
US 2018/0282661 A1    Oct. 4, 2018

(30) Foreign Application Priority Data
Oct. 1, 2015   (EP) .................................. 15187846

(51) Int. Cl.
*C11B 9/00* (2006.01)
*C07C 49/553* (2006.01)

(52) U.S. Cl.
CPC .......... *C11B 9/0053* (2013.01); *C07C 49/553* (2013.01); *C07B 2200/09* (2013.01); *C07C 2602/28* (2017.05)

(58) Field of Classification Search
CPC .................................................... C07C 49/553
See application file for complete search history.

(56) References Cited

U.S. PATENT DOCUMENTS 4,396,670 A    8/1983  Sinclair

FOREIGN PATENT DOCUMENTS

WO    WO 2001/041915 A1    6/2001
WO    WO 2006/086908 A1    8/2006

OTHER PUBLICATIONS

International Search Report and Written Opinion, application PCT/EP2016/073267 dated Oct. 27, 2016.
Belhassen et al., 'Volatile constituents of vetiver: a review', Flavour & Fragrance Journal, 2015, vol. 30, pp. 26-82.
Dietrich et al., 'Amino resin microcapsules, IV. Surface tension of the resins and mechanism of capsule formation', Acta Polymerica, vol. 41 (1990), No. 2, pp. 91-95.
Dietrich et al., 'Amino resin microcapsules, I. Literature and patent review', Acta Polymerica, vol. 40 (1989), n° 4, pp. 243-251.
Bone et al., 'Microencapsulated Fragrances in Melamine Formaldehyde Resins', Chimia, 2011, vol. 65, n° 3, pp. 177-181.
Lee et al., 'Microencapsulation of fragrant oil via in situ polymerization . . . ', Journal of Microencapsulation, 2002, vol. 19(5), pp. 559-569.
Still et al., 'A Simple Synthesis of trans-8,10-Dimethyl-1(9)-octal-2-one via an acid-catalyzed Michael reaction', J. Org. Chem. (1977) vol. 42, pp. 1258-1259.
Caine et al., 'Metal-Ammonia Reduction of cis-8,10-Dimethyl-(9)-octal-2-one', J. Org. Chem. (1978), vol. 43, pp. 755-757.
Revial G., 'Asymmetric Michael-type Alkylation of Chiral Imines . . . ' Tetrahedron Letters (1989), vol. 30, No. 31, pp. 4121-4124.
Maurer et al, '235. Zur Kenntnis der sesquiterpenoiden . . . ',1972, Helvetica, Chimica Acta, vol. 55, pp. 2371-2382 (see English abstract).
Belhassen et al., "Unravelling the Scent of Vetiver: Identification of Character-Impact Compounds", Chem Biodivers., Published Nov. 18, 2014, pp. 1821-1842, vol. 11, No. 11.
Bella et al., "Chemistry of odorants: stereoselective synthesis of octahydronaphthalene-based perfumery Georgywood, (+,-)-1-[(1R*,2S*)-1,2,3,4,5,6,7,8-octahydro-1,2,8,8-tetramethylnaphthalen-2-yl]ethan-1-one", Tetrahedron, Published Apr. 21, 2004, pp. 4821-4827, vol. 60, No. 22.

*Primary Examiner* — Arrie L Reuther
(74) *Attorney, Agent, or Firm* — Armstrong Teasdale LLP

(57) ABSTRACT

The present invention relates to trans isomers of formula (I)

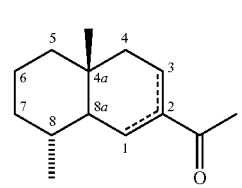

(I)

in the form of any one of its stereoisomers or a mixture thereof, and wherein the bold and hatched lines indicate a relative or absolute configuration; and one dotted line represents a carbon-carbon single bond and the other a carbon-carbon double bond;
and their uses as perfuming ingredients (e.g. to impart vetiver/rooty notes), e.g. in consumer products.

10 Claims, No Drawings

VETIVER ODORANT

RELATED APPLICATIONS

This application is a national stage application under 35 U.S.C. § 371 filing of International Patent Application PCT/EP2016/073267, filed Sep. 29, 2016, which claims the benefit of European patent application n° 15187846.9 filed Oct. 1, 2015.

TECHNICAL FIELD

The present invention relates to the field of perfumery. More particularly, it concerns trans isomers of formula (I) as defined herein below, and their uses as perfuming ingredients, e.g. in consumer products.

BACKGROUND

To the best of our knowledge the compounds of formula (I), which are all derivatives having an anti-configuration between the two methyl groups at carbon 4a and 8, are novel.

To the best of our knowledge, the only analogue reported in the literature, and described for its odor properties, is 1-[(4aRS,8SR,8aSR)-4a,8-dimethyl-3,4,4a,5,6,7,8,8a-octahydro-2-naphthalenyl]ethanone, i.e a derivative having a syn configuration between the two methyl groups at carbon 4a and 8 (see N. Baldovini et al, in *Flavour Frag. J.*, 2015, 30, 26). Said prior analogue has been defined in nature and described has having a woody-fruity damascene odor, i.e. significantly different from the any one of the present compounds.

This document does not report or suggest any organoleptic properties of the compounds of formula (I), or any use of said compounds in the field of perfumery.

DESCRIPTION OF THE INVENTION

We have now surprisingly discovered that a compound of formula

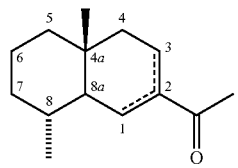

(I)

in the form of any one of its stereoisomers or a mixture thereof, and wherein the bold and hatched lines indicate a relative or absolute configuration; and
one dotted line represents a carbon-carbon single bond and the other a carbon-carbon a double bond;
can be used as perfuming ingredient, for instance to impart odor notes of the vetiver/rooty type.

For the sake of clarity, by the expression "any one of its stereoisomers", or the similar, it is meant the normal meaning understood by a person skilled in the art, i.e. that the invention's compound can be a pure enantiomer (if chiral) or diastereomer (e.g. the hydrogen atom on the carbon 8a in a syn or anti conformation relative to the methyl group in position 4a), provided of course that the two methyl groups at carbon 4a and 8 are in an anti-configuration either relative or absolute.

For the sake of clarity, by the expression "the bold and hatched lines indicate a relative or absolute configuration" or the similar, it is meant the normal meaning understood by a person skilled in the art, i.e. that in the case of an relative configuration compound (I) is in the form of a mixture of stereoisomers comprising more than 50% (w/w) of the (4aRS,8RS) stereoisomer, i.e. a compound having the two methyl groups in a relative trans configuration as shown in formula (I), or in the case of an absolute configuration compound (I) is in the form of a mixture of stereoisomers comprising more than 50% (w/w) of the (4aS,8S) stereoisomer.

For the sake of clarity, by the expression "wherein one dotted line represents a carbon-carbon single bond and the other a carbon-carbon double bond", or the similar, it is meant the normal meaning understood by a person skilled in the art, i.e. that the whole bonding (solid and dotted line) between the carbon atoms connected by said dotted line, e.g. carbon 1 and 2, is a carbon-carbon single or double bond.

According to a particular embodiment of the invention, compound (I) can be a compound of formula

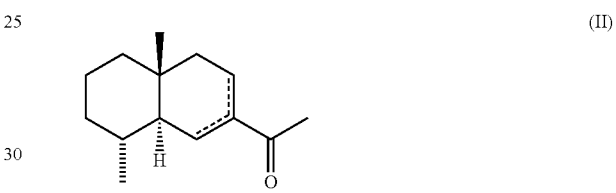

(II)

wherein the bold, hatched and dotted lines have the meaning indicated in formula (I).

According to a particular embodiment of the invention, compound (I) can be a compound of formula

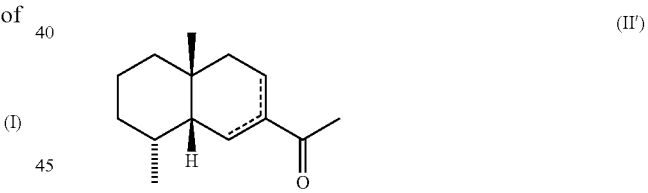

(II')

wherein the bold, hatched and dotted lines have the meaning indicated in formula (I).

In the present invention the term "compound of formula (I)" is constructed in order in encompassing also all composition of matter resulting from the admixture of at least two chemicals responding to formula (I). In particular, said compound of formula (I) can be in the form of a composition of matter comprising, or consisting of:
  at least 55% w/w of the compound of formula (II'); and
  at most 45% w/w of the compound of formula (II).

Moreover, said compound of formula (I) can be in the form of a composition of matter comprising, or consisting of:
  at most 55% w/w of the compound of formula (II'); and
  at least 45% w/w of the compound of formula (II).

Moreover, said compound of formula (I) can be in the form of a composition of matter comprising, or consisting of:
  at most 40% w/w of the compound of formula (II'); and
  at least 60% w/w of the compound of formula (II).

Preferably, said compound of formula (I) can be in the form of a composition of matter comprising, or consisting of:

at most 20% w/w of the compound of formula (II'); and
at least 80% w/w of the compound of formula (II).

As specific examples of the invention's compounds, one may cite, as non-limiting example, a 15:85 mixture of 1-[(4aRS,8RS,8aRS)-4a,8-dimethyl-3,4,4a,5,6,7,8,8a-octahydro-2-naphthalenyl]ethanone and 1-[(4aRS,8RS,8aSR)-4a,8-dimethyl-1,4,4a,5,6,7,8,8a-octahydro-2-naphthalenyl]ethanone (herein after referred to as Mix 1) which has a very powerful and warm characteristic vetiver, rooty odor comprising some powdery/iris and ambery aspects. For the sake of clarity it is understood that that by "15:85 mixture", or the similar, it is meant a mixture of the two stereoisomers in the weight ratio of 15 to 85.

As another example, one may cite a 1:1 mixture of 1-[(4aRS,8RS,8aSR)-4a,8-dimethyl-3,4,4a,5,6,7,8,8a-octahydro-2-naphthalenyl]ethanone and 1-[(4aRS,8RS,8aRS)-4a,8-dimethyl-1,4,4a,5,6,7,8,8a-octahydro-2-naphthalenyl]ethanone (herein after referred to as Mix 2) which has a characteristic vetiver, rooty odor comprising some ionone and camphor aspects.

As another example, one may cite a mixture containing 45% of Mix 1 and 55% of Mix 2 (herein after referred to as Mix 3), the percentage being expressed on a w/w basis, which possesses a very good, powerful and warm characteristic vetiver, rooty odor comprising some powdery and iris aspects.

As other specific, but non-limiting, examples of the invention's compounds, one may cite the following ones in Table 1:

TABLE 1

Invention's compounds structures and their odor properties

| Compound structure and name | Odor notes |
|---|---|
| 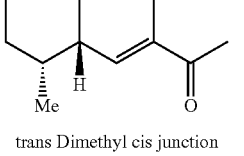<br>Mix 1 (as defined in Example 1.2) | See above: vetiver/rooty odor |

TABLE 1-continued

Invention's compounds structures and their odor properties

| | Odor notes |
|---|---|
| 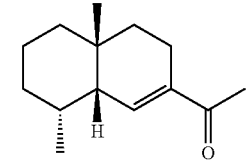<br>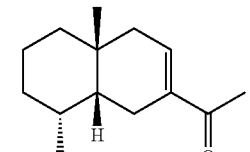<br>Mix 2 (as defined in Example 1.3) | See above: vetiver/rooty odor |
| 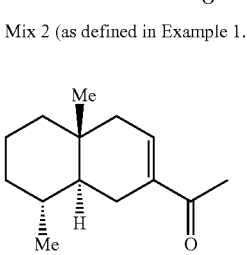<br>trans Dimethyl trans junction<br>β-enone (see Example 1.2.c) | Very good vetiver, rooty, powdery |
| 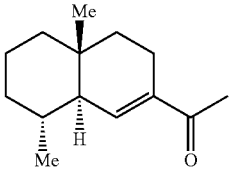<br>trans Dimethyl trans junction<br>α-enone (see Example 1.2.c) | Vetiver, rooty, powdery, ambery, very powerful |
| 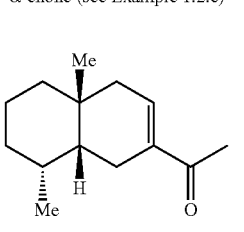<br>trans Dimethyl cis junction<br>β-enone (see Example 1.3.b) | Vetiver but camphor, earthy, powerful |
| 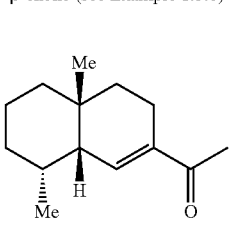<br>trans Dimethyl cis junction<br>α-enone (see Example 1.3.b) | Vetiver, rooty, natural |

Prior art compound

TABLE 1-continued

Invention's compounds structures and their odor properties

Odor notes

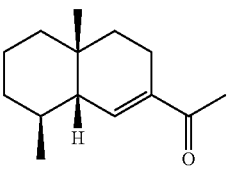

Cedar/woody, fruity/grapefruit odor

1-[(4aRS,8SR,8aSR)-4a,8-dimethyl-
3,4,4a,5,6,7,8,8a-octahydro-2-
naphthalenyl]ethanone According to a particular embodiment of the invention, the compounds of formula (I) are 1-[(4aRS,8RS,8aRS)-4a,8-dimethyl-3,4,4a,5,6,7,8,8a-octahydro-2-naphthalenyl]ethanone, 1-[(4aRS,8RS,8aSR)-4a,8-dimethyl-1,4,4a,5,6,7,8,8a-octahydro-2-naphthalenyl]ethanone, 1-[(4aRS,8RS,8aSR)-4a,8-dimethyl-3,4,4a,5,6,7,8,8a-octahydro-2-naphthalenyl]ethanone, 1-[(4aRS,8RS,8aRS)-4a,8-dimethyl-1,4,4a,5,6,7,8,8a-octahydro-2-naphthalenyl]ethanone and/or mixtures thereof.

When the odor of the invention's compounds is compared with that of the prior art compound 1-[(4aRS,8SR,8aSR)-4a,8-dimethyl-3,4,4a,5,6,7,8,8a-octahydro-2-naphthalenyl]ethanone (i.e. the cis compound), then the invention's compounds distinguish themselves by the type of the woody note and the type of the other odor notes associated.

The woody note associated with the invention's compounds is of the rooty type, i.e. a warm heavy effect, while the woody note associated with the prior art compounds is of the cedar type, i.e. a resin, sawdust, fresh effect. The odor of the invention's compounds distinguish also from the prior art by lacking, or not possessing significant, fruity notes, which are characteristic of the prior art compound. Moreover, the odor of the prior art's compound distinguishes also from the present invention by lacking, or not possessing significant, iris/powdery notes, which are characteristic of the invention's compounds.

Said differences, besides being not foreseeable, lend the invention's compounds and the prior art compound to be each suitable for different uses, i.e. to impart different organoleptic impressions.

As mentioned above, the invention concerns the use of a compound of formula (I) as perfuming ingredient. In other words, it concerns a method to confer, enhance, improve or modify the odor properties of a perfuming composition or of a perfumed article or of a surface, which method comprises adding to said composition or article an effective amount of at least a compound of formula (I), e.g. to impart its typical note.

By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycols, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

As solid carrier it is meant a material where the perfuming composition or some element of the perfuming composition can be chemically or physically bound. In general such solid carriers are employed either to stabilize the composition, either to control the rate of evaporation of the compositions or of some ingredients. The employment of solid carriers is of current use in the art and a person skilled in the art knows how to reach the desired effect. However by way of non-limiting example as solid carriers one may cite absorbing gums or polymers or inorganic material, such as porous polymers, cyclodextrines, wood based materials, organic or inorganic gels, clays, gypsum talc or zeolites.

As other non-limiting examples of solid carrier one may cite encapsulating materials. Examples of such materials may comprise of wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique. As non-limiting examples one may cite in particular the core-shell encapsulation with resins of the aminoplast, polyamide, polyester, polyurea or polyurethane type or a mixture thereof (all of said resins are well known to a person skilled in the art) using techniques like phase separation process induced by polymerization, by interfacial polymerization, by coacervation or altogether (all of said techniques have been described in the prior art), and optionally in presence of polymeric stabilizer or a cationic copolymer.

In particular, as resins one may cite the ones produced by the polycondensation of an aldehyde (e.g. formaldehyde, 2,2-dimethoxyethanal, glyoxal, glyoxylic acid or glycolaldehyde and mixtures thereof) with an amine, namely urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

In particular, as resins one may cite the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins, with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinency, which also address the suitable uses of such microcapsules, are represented for example by the article of H. Y. Lee et al. in Journal of Microencapsulation, 2002, vol. 19, pages 559-569, international patent publication WO 01/41915 or yet the article of S. Bone et al. in Chimia, 2011, vol. 65, pages 177-181.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:
Aldehydic ingredients: decanal, dodecanal, 2-methyl-undecanal, 10-undecenal, octanal and/or nonenal;
Aromatic-herbal ingredients: eucalyptus oil, camphor, eucalyptol, menthol and/or alpha-pinene;
Balsamic ingredients: coumarine, ethylvanillin and/or vanillin;
Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
Floral ingredients: methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methyl-ionones isomers;
Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;
Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;
Musk ingredients: 1,4-dioxa-5,17-cycloheptadecane-dione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;
Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2, 2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3, 4,6,7,8,8a-octahydronaphthalen-2-yl)ethan-1-one and/or isobornyl acetate;
Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), color agents (e.g. dyes and/or pigments), preservative (e.g. antibacterial or antimicrobial or antifungi or anti irritant agents), abrasives, skin cooling agents, fixatives, insect repellants, ointments, vitamins and mixture thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his/her work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as a perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's compound. For the sake of clarity, said perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be a perfume, such as a fine perfume, a splash or eau de perfume, a cologne or an shave or after-shave lotion; a fabric care product, such as a liquid or solid detergent, a fabric softener, a fabric refresher, an ironing water, a paper, or a bleach, carpet cleaners, curtain-care products; a body-care product, such as a hair care product (e.g. a shampoo, a coloring preparation or a hair spray, a color care product, hair shaping product, a dental care product), a disinfectant, an intimate care product; a cosmetic preparation (e.g. a skin cream or lotion, a vanishing cream or a deodorant or antiperspirant (e.g. a spray or roll on), hair remover, tanning or sun or after sun product, nail products, skin cleansing, a makeup); or a skin-care product (e.g. a perfumed soap, shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, furnisher care, wipe, a dish detergent or hard-surface (e.g. a floor, bath, sanitary or a windows) detergent; a leather care product; a car care product, such as a polish, waxes or a plastic cleaners.

Some of the above-mentioned perfuming consumer product may represent an aggressive medium for the invention's compound, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 1% to 50% by weight, or even more, of the compounds of the invention based on the weight of the composition into which they are incorporated. Concentrations lower than these, such as in the order of 0.1% to 20% by weight, can be used when these compounds are incorporated into perfuming consumer products, percentage being relative to the weight of the article.

EXAMPLES

The invention will now be described in further detail by way of the following examples, wherein the abbreviations have the usual meaning in the art, the temperatures are indicated in degrees centigrade (° C.); NMR spectra were acquired using either a Bruker Avance II Ultrashield 400 plus operating at 400 MHz, ($^1$H) and 100 MHz ($^{13}$C) or a Bruker Avance III 500 operating at 500 MHz ($^1$H) and 125 MHz ($^{13}$C) or a Bruker Avance III 600 cryoprobe operating at 600 MHz ($^1$H) and 150 MHz ($^{13}$C), the chemical shifts δ are indicated in ppm with respect to TMS as standard, the coupling constants J are expressed in Hz.

Example 1

Synthesis of Compounds of Formula (I)
1) Preparation of Mix 3
A mixture of 95/5 of (4aRS,8RS)-4a,8-dimethyl-4,4a,5, 6,7,8-hexahydronaphthalen-2(3H)-one and (4aRS,8SR)-4a, 8-dimethyl-4,4a,5,6,7,8-hexahydronaphthalen-2(3H)-one was prepared according to W. C. Still and F. L. vanMiddelsworth, *J. Org. Chem.*, 1977, 42, 1258.

Separation of said 95:5 mixture (1967 g) via vacuum distillation using a Sulzer DX column (1.2 M), at 0.1 mbar gave mixed fractions containing the cis dimethyl minor compound, then the pure trans dimethyl enone ((4aRS,8RS)-4a,8-dimethyl-4,4a,5,6,7,8-hexahydronaphthalen-2(3H)-one) b.p. 77-87° C. (1462 g)

$^1$H and $^{13}$C NMR spectra were in good agreement with literature values. (*J. Org. Chem.*, 1978, 43, 755. *Helv. Chim. Acta.*, 1972, 55, 2371.)

Both enantiomers of the enone could be prepared following G. Devial, *Tetrahedron Lett.*, 1989, 30, 4121.

a) Hydrogenation of Pure Trans Dimethyl Enone to Give the Decalone

In an autoclave, a suspension of 10% palladized charcoal (0.2 g) and the trans dimethyl enone obtained above (13.0 g, 72.9 mmol) was evacuated then purged 3 times with hydrogen gas and stirred under an atmosphere of hydrogen gas (60 bars) for 5 hours at ambient temperature. The suspension was filtered through a small plug of celite, rinsed with diethyl ether and the solvents removed in vacuo. The crude ketone was further purified by bulb to bulb distillation 160° C. at 0.1 mbar to give the decalone as a mixture of cis and trans junction stereoisomers (6:4, cis:trans), 12.0 g, 91%. This mixture was used as such in the next steps.

For sake of clarity: cis junction stereoisomer is (4aRS, 8RS,8aRS)-4a,8-dimethyloctahydronaphthalen-2(1H)-one and trans junction stereoisomer is (4aRS,8RS,8aSR)-4a,8-dimethyloctahydronaphthalen-2(1H)-one.

b) Acetylide Addition to the Enone Mixture Obtained Under a)

A solution of the dimethyl decalone obtained above under a) (74 g, 0.278 mol) in THF (60 mL) was added slowly dropwise to a stirred solution of ethynyl magnesium bromide (0.5 M in THF, 1070 mL, 0.534 mol) cooled to 4° C. in an ice bath. The solution was allowed to warm to ambient temperature and stirred overnight. The reaction mixture was poured into ice and extracted with diethyl ether, the organic phase washed with saturated NH$_4$Cl solution, then brine, dried over Na$_2$SO$_4$, filtered and the solvents removed in vacuo to yield the crude propargylic alcohol, 85 g as a brown oil. Further purification by vacuum distillation with a 15 cm Vigreux column, 0.1 mbar, b.p 72°-85° gave the propargylic alcohol as a colorless oil and a complex mixture of isomers, 58.5 g (82% yield). The complex mixture of stereoisomeric propargylic alcohols was used without further purification in the next step.

c) Rupe Rearrangementon the Acetylene Derivative Obtained Under b)

The mixture of propargylic alcohols (58.0 g, 0.28 mol) was dissolved in formic acid (560 mL, 95%) and heated at 90° C. for 2 hours then cooled and poured into a mixture of ice and water. The aqueous phase was extracted with pentane, the organic phase washed with water, then saturated NaHCO$_3$ solution, brine, dried over Na$_2$SO$_4$, filtered and the solvents removed in vacuo to yield the crude final enone as a mixture of isomers, 60.5 g. Further purification by vacuum distillation with a Vigreux column, 0.05 mbar, b.p. 81-89° C., gave the enone Mix 3 as a mixture of isomers, 45.8 g, 79% yield. Stereoisomer ratio, 28:9:35:28=100.

Trans di methyl, cis junction: 56%
28%=1-((4aSR,8SR,8aRS)-4a,8-dimethyl-3,4,4a,5,6,7,8, 8a-octahydronaphthalen-2-yl)ethan-1-one
28%=1-((4aSR,8SR,8aRS)-4a,8-dimethyl-1,4,4a,5,6,7,8, 8a-octahydronaphthalen-2-yl)ethan-1-one Trans di methyl, trans junction: 44%
9%=1-((4aSR,8SR,8aSR)-4a,8-dimethyl-3,4,4a,5,6,7,8, 8a-octahydronaphthalen-2-yl)ethan-1-one
35%=1-((4aSR,8SR,8aRS)-4a,8-dimethyl-1,4,4a,5,6,7,8, 8a-octahydronaphthalen-2-yl)ethan-1-one For the identity and structural elucidation of the individual isomers vide infra.

2) Preparation of Mix 1
a) Hydrogenation of Pure Trans Dimethyl Enone to Give the Decalone The mixture of pure saturated cis and trans junction stereoisomers decalones obtained under 1.a) was separated by fractional distillation using a 1.2 M Fischer column, with a condenser heated to 50° C., 1 mbar. It was thus obtained: (4aRS,8RS,8aRS)-4a,8-dimethyloctahydronaphthalen-2 (1H)-one (trans junction decalone isomer) 29.2 g (98.2% GC) b.p 68-69° C.

$^1$H and $^{13}$C NMR spectra were in good agreement with literature values. (*J. Org. Chem.*, 1978, 43, 755. *Helv. Chim. Acta.*, 1972, 55, 2371.)

(4aRS,8RS,8aRS)-4a,8-dimethyloctahydronaphthalen-2 (1H)-one (cis junction decalone isomer) 32.3 g (99.8% GC) b.p 69-70° C. plus enriched fractions.

$^1$H and $^{13}$C NMR spectra were in good agreement with literature values. (*J. Org. Chem.*, 1978, 43, 755. *Helv. Chim. Acta.*, 1972, 55, 2371.)

b) Acetylide Addition to the Enone Mixture Obtained Under 2.a)

A solution of the dimethyl decalone (contained under 2.a), pure trans isomer, 7.0 g, 38.8 mmol) in THF (75 mL) was treated according to general procedure under 1.b) to yield the crude propargylic alcohol as a mixture of isomers, 8.1 g as a brown oil which was used directly in the next step without further purification.

c) Rupe Rearrangementon the Acetylene Derivative Obtained Under 2. b)

The mixture of propargylic alcohols (obtained under 2.b), 8.0 g, 38.8 mmol) was dissolved in formic acid (80 mL) and heated according to the procedure under 1.c) to yield the crude enone as a mixture of isomers (15:85), 7.9 g as brown oil. Further purification by bulb to bulb vacuum distillation, 0.1 mbar, 105° C., gave the enone as a mixture of isomers (15:85), 5.9 g, 74% yield.

15%=trans dimethyl trans junction α-enone stereoisomer=1-((4aSR,8SR,8aSR)-4a,8-dimethyl-3,4,4a,5,6,7,8,8a-octahydronaphthalen-2-yl)ethan-1-one:

$^1$H-NMR: 6.90 (d, J 1.3, 1H), 2.32 (dq, J 6.7, 1.4 1H), 2.29 (s, 3H), 2.27-2.16 (m, 1H), 1.82-1.76 (m, 1H), 1.68 (dt, J 13.5, 4.2, 1H), 1.63-1.42 (m, 6H), 1.32 (td, J 12.5, 7, 1H), 1.15 (td, J 13.1, 4.3, 1H), 1.01 (d, J 6.4, 3H), 0.75 (s, 3H)

$^{13}$C-NMR: 199.6 (s), 140.3 (d), 138.8 (s), 51.8 (d), 40.0, 37.5, 36.8 (t), 32.6 (s), 29.6 (d), 25.3 (q), 21.4, 21.1 (t), 19.7 (q), 16.2 (q)

85%=trans dimethyl trans junction β-enone stereoisomer=1-((4aSR,8SR,8aRS)-4a,8-dimethyl-1,4,4a,5,6,7,8,8a-octahydronaphthalen-2-yl)ethan-1-one:

¹H-NMR: 6.85 (bs, 1H), 2.58 (dd, J 17.9, 4.8 1H), 2.29 (s, 3H), 2.01 (bs, 1H), 1.72-1.48 (m, 5H), 1.38-1.27 (m, 1H), 1.18-1.08 (m, 1H), 1.03-0.91 (m, 2H), 1.00 (d, J 6.4, 3H), 0.77 (s, 3H)

¹³C-NMR: 199.3 (s), 139.6 (d), 139.0 (s), 46.1 (d), 43.3, 41.1, 36.1 (t), 32.6 (d), 32.0 (s), 25.2 (q), 24.9, 21.6 (t), 20.1, 17.5 (q)

3) Preparation of Mix 2 a) Acetylide Addition to the Enone Mixture Obtained Under 3.a)

A solution of the dimethyl cis decalone (pure cis junction stereoisomer, obtained under 2.a), 14 g, 73 mmol) was treated as per the procedure under 1.b) to yield the crude propargylic alcohol as a mixture of isomers, 18 g as a brown oil.

b) Rupe Rearrangement of the Acetylene Derivative Obtained Under 3.b)

The mixture of propargylic alcohols (obtained under 3.a), 7.7 g, 37.4 mmol) was dissolved in formic acid (75 mL) and treated according to the procedure under 1.c) to yield the crude enone as a mixture of isomers, 6.05 g.

Further purification by bulb to bulb vacuum distillation, 0.05 mbar, 145° C., gave the enone as a mixture of isomers (1:1), 5.2 g, 67% yield.

The two isomers were further purified and separated by fractional distillation using a Fischer column (50 cm) 1 mbar gave the pure isomers.

trans dimethyl cis junction α-enone stereoisomer=1-((4aSR,8SR,8aRS)-4a,8-dimethyl-3,4,4a,5,6,7,8,8a-octahydronaphthalen-2-yl)ethan-1-one:

¹H-NMR: 6.85 (bd, 1H), 2.36-2.30 (m, 1H), 2.30 (s, 3H), 2.18-2.10 (m, 1H), 2.08-2.01 (m, 1H), 1.98 (bs, 1H), 1.53 (ddd, J 13.2, 6.1, 1.0, 1H), 1.48 (ddt, J 10, 6.7, 3.4, 1H), 1.46-1.41 (bd, 1H), 1.38 (ddd, J 12.9, 12.7, 6.4, 1H), 1.30 (ddd, J 13.2, 10.3, 7.6, 1H), 1.05 (d, J 7, 3H), 1.03 (s, 3H), 0.99-0.95 (bd, 1H), 0.81 (ddq, J 12.8, 9.7, 6.5, 1H).

¹³C-NMR: 199.4 (s), 140.4 (d), 139.7 (s), 47.6 (d), 36.6 (t), 32.0 (s), 30.8 (t), 30.2 (t), 29.6 (t), 26.4 (q), 25.4 (q), 21.8 (t), 20.3 (t), 19.5 (q)

trans dimethyl cis junction β-enone stereoisomer=1-(4aSR,8SR,8aSR)-4a,8-dimethyl-1,4,4a,5,6,7,8,8a-octahydronaphthalen-2-yl)ethan-1-one:

¹H-NMR: 6.83-6.79 (m, 1H), 2.29 (s, 3H), 2.28-2.24 (m, 1H), 2.20-2.14 (m, 1H), 2.09-1.96 (m, 3H), 1.58 (dt, J 13.4, 4.6, 1H), 1.54 (dt, J 13.3, 4.6, 1H), 1.51-1.35 (m, 3H), 1.32 (td, J 13.3, 4.6, 1H), 1.22 (qd, J 13.0, 5.0, 1H), 1.04 (s, 3H), 0.95-0.90 (m, 1H), 0.89 (d, J 6.9, 3H)

¹³C-NMR: 199.4 (s), 139.2 (d), 137.8 (s), 42.2 (t), 41.8 (d), 32.0 (s), 30.9 (t), 29.2 (d), 27.7 (t), 26.2 (q), 25.2 (q), 21.5 (t), 19.5 (t)

Example 2

Preparation of a Perfuming Composition

A perfuming composition, of the woody type, was prepared by admixing the following ingredients:

| Parts by weight | Ingredient |
|---|---|
| 200 | Ambrox ® ¹⁾ |
| 400 | Bergamot oil |
| 40 | 10%* 7-Methyl-2H,4H-1,5-benzodioxepin-3-one |
| 20 | Cardamon oil |

-continued

| Parts by weight | Ingredient |
|---|---|
| 600 | Lemon oil |
| 100 | Coumarin |
| 20 | Alpha damascone |
| 200 | (1'R,E)-2-ethyl-4-(2',2',3'-trimethyl-3'-cyclopenten-1'-yl)-2-buten-1-ol |
| 1000 | Dihydromyrcenol |
| 200 | (1-Ethoxyethoxy)cyclododecane |
| 200 | Hedione ® ²⁾ HC |
| 200 | 3-(1,3-Benzodioxol-5-yl)-2-methylpropanal |
| 200 | Helvetolide ® ³⁾ |
| 200 | Iralia ® ⁴⁾ Total |
| 20 | Nutmeg oil |
| 2000 | Hedione ® ⁵⁾ |
| 10 | Neobutenone ® ⁶⁾ Alpha |
| 20 | Pink pepper oil |
| 100 | Nirvanol ® ⁷⁾ |
| 100 | (Z)-3-Hexen-1-ol salicylate |
| 10 | 2-Ethyl-4,4-dimethylcyclohexanone |
| 60 | Vetiver oil |
| 100 | (+)-8,13:13,20-Diepoxy-15,16-dinorlabdane |
| 6000 | |

¹⁾ (−)-(8R)-8,12-epoxy-13,14,15,16-tetranorlabdane ᵃ⁾
²⁾ high cis methyl dihydrojasmonate ᵃ⁾
³⁾ (1S,1'R)-2-[1-(3',3'-dimethyl-1'-cyclohexyl)ethoxy]-2-methylpropyl propanoate ᵃ⁾
⁴⁾ mixture of methylionones isomers ᵃ⁾
⁵⁾ methyl dihydrojasmonate ᵃ⁾
⁶⁾ 1-(5,5-dimethyl-1-cyclohexen-1-yl)-4-penten-1-one ᵃ⁾
⁷⁾ 3,3-dimethyl-5-(2,2,3-trimethyl-3-cyclopenten-1-yl)-4-penten-2-ol ᵃ⁾
*in dipropyleneglycol
ᵃ⁾ origin: Firmenich SA, Geneva, Switzerland The addition of 4000 parts by weight of Mix 3 (as defined in Example 1.1) to the above-described composition imparted to the latter a reinforced the rooty/powdery characters by blending very well with both woody-vetiver (Vetiver oil) and powdery-violet (Iralia® Total) elements present in the original formula.

When instead of Mix 3 was added the same amount of Mix 1 (as defined in Example 1.2), then said ingredient provided a similar effect to the one of Mix 3, but added also a more pronounced push of the dark woody-vetiver element of the formula.

When instead of Mix 3 was added the same amount of Mix 2 (as defined in Example 1.3), then said ingredient provided a similar effect to the one of Mix 3, but added also a more pronounced push of the powdery-violet element of the formula.

When instead of Mix 3 was added the same amount of prior art's 1-[(4aRS,8SR,8aSR)-4a,8-dimethyl-3,4,4a,5,6,7,8,8a-octahydro-2-naphthalenyl]ethanone, then this ingredient pushed the fruity-Dasmascone (Damascone Alpha) element (an element not observed with the invention's compounds) and twists the woody accord in a more cedar like direction.

The invention claimed is:
1. A compound of formula

(I)

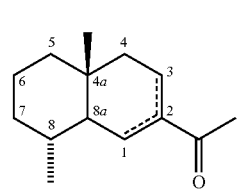

in the form of any one of its stereoisomers or a mixture thereof, wherein the methyl groups at carbon 4a and 8 are in an anti-configuration either relative or absolute, and wherein the bold and hatched lines indicate a relative or absolute configuration; and one dotted line represents a carbon-carbon single bond and the other a carbon-carbon double bond;

wherein the compound has odor notes comprising a vetiver odor.

2. The compound of claim 1, characterized in that it is a compound of formula

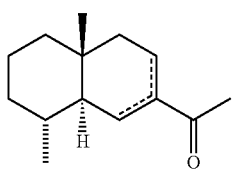

(II)

wherein the bold, hatched and dotted lines have the meaning indicated in claim 1.

3. A method to confer, enhance, improve or modify the odor properties of a perfuming composition or of a perfumed article, which method comprises adding to said composition or article an effective amount of at least a compound of formula (II) as defined in claim 2.

4. The compound of claim 1, characterized in that it is 1-[(4aRS,8RS,8aRS)-4a,8-dimethyl-3,4,4a,5,6,7,8,8a-octahydro-2-naphthalenyl]ethanone, 1-[(4aRS,8RS,8aSR)-4a,8-dimethyl-1,4,4a,5,6,7,8,8a-octahydro-2-naphthalenyl]ethanone, 1-[(4aRS,8RS,8aSR)-4a,8-dimethyl-3,4,4a,5,6,7,8,8a-octahydro-2-naphthalenyl]ethanone, 1-[(4aRS,8RS,8aRS)-4a,8-dimethyl-1,4,4a,5,6,7,8,8a-octahydro-2-naphthalenyl]ethanone or mixtures thereof.

5. A perfuming composition comprising
i) at least one compound of formula (I), as defined in claim 1;
ii) at least one ingredient selected from the group consisting of a perfumery carrier and a perfumery base; and
iii) optionally at least one perfumery adjuvant.

6. A perfumed consumer product comprising at least one compound of formula (I), as defined in claim 1.

7. A perfumed consumer product according to claim 6, characterized in that the perfumed consumer product is a perfume, a fabric care product, a body-care product, a cosmetic preparation, a skin-care product, an air care product or a home care product.

8. A perfuming consumer product according to claim 6, characterized in that the perfumery consumer product is a fine perfume, a splash or eau de perfume, a cologne, a shave or after-shave lotion, a liquid or solid detergent, a fabric softener, a fabric refresher, an ironing water, a paper, a bleach, a carpet cleaners, curtain-care products, a shampoo, a coloring preparation, a color care product, a hair shaping product, a dental care product, a disinfectant, an intimate care product, a hair spray, a vanishing cream, a deodorant or antiperspirant, hair remover, tanning or sun product, nail products, skin cleansing, a makeup, a perfumed soap, shower or bath mousse, oil or gel, foot/hand care products, a hygiene product, an air freshener, a "ready to use" powdered air freshener, a mold remover, furnisher care, wipe, a dish detergent or hard-surface detergent, a leather care product, or a car care product.

9. A method to confer, enhance, improve or modify the odor properties of a perfuming composition or of a perfumed article, which method comprises adding to said composition or article an effective amount of at least a compound of formula (I) as defined in claim 1.

10. The compound of claim 9, wherein the compound is 1-[(4aRS,8RS,8aRS)-4a,8-dimethyl-3,4,4a,5,6,7,8,8a-octahydro-2-naphthalenyl]ethanone, 1-[(4aRS,8RS,8aSR)-4a,8-dimethyl-1,4,4a,5,6,7,8,8a-octahydro-2-naphthalenyl]ethanone, 1-[(4aRS,8RS,8aSR)-4a,8-dimethyl-3,4,4a,5,6,7,8,8a-octahydro-2-naphthalenyl]ethanone, 1-[(4aRS,8RS,8aRS)-4a,8-dimethyl-1,4,4a,5,6,7,8,8a-octahydro-2-naphthalenyl]ethanone or mixtures thereof.

* * * * *